(12) United States Patent
Davis

(10) Patent No.: US 6,304,712 B1
(45) Date of Patent: *Oct. 16, 2001

(54) BENDABLE ILLUMINATING APPLIANCE

(76) Inventor: James M. Davis, 4687 Pond Apple Dr. South, Naples, FL (US) 33999

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/187,372

(22) Filed: Nov. 6, 1998

Related U.S. Application Data

(60) Provisional application No. 60/064,728, filed on Nov. 6, 1997.

(51) Int. Cl.[7] ............................... A61C 1/00; G02B 6/00
(52) U.S. Cl. ........................... 385/147; 433/29; 606/16
(58) Field of Search ........................ 385/147, 31, 32, 385/50, 51, 52, 117, 121; 433/29, 141, 147; 606/13–16

(56) References Cited

U.S. PATENT DOCUMENTS

| | | | | |
|---|---|---|---|---|
| 3,589,800 | * | 6/1971 | Cardona ................................ | 385/147 |
| 3,641,332 | * | 2/1972 | Reick et al. ........................ | 385/142 |
| 3,801,181 | * | 4/1974 | Kitano et al. ........................ | 359/672 |
| 4,422,719 | * | 12/1983 | Orcutt ................................. | 385/123 |
| 5,228,852 | * | 7/1993 | Goldsmith et al. ..................... | 433/29 |
| 5,851,112 | * | 12/1998 | Daikuzono et al. .................... | 433/29 |
| 5,999,687 | * | 12/1999 | Abraham et al. ....................... | 385/33 |

\* cited by examiner

*Primary Examiner*—Hemang Sanghavi
(74) *Attorney, Agent, or Firm*—William E. Noonan

(57) ABSTRACT

A bendable medical, dental and surgical illuminating appliance is disclosed. The appliance includes a light-conducting rod, at least a portion of which is light projecting. The rod is flexible and comprises a self-sustaining shape. The rod also includes a light inlet that is operably engaged with the outlet of a fiberoptic conductor. The opposite, inlet end of the conductor is optically interengaged with a fiberoptic illuminator.

13 Claims, 3 Drawing Sheets

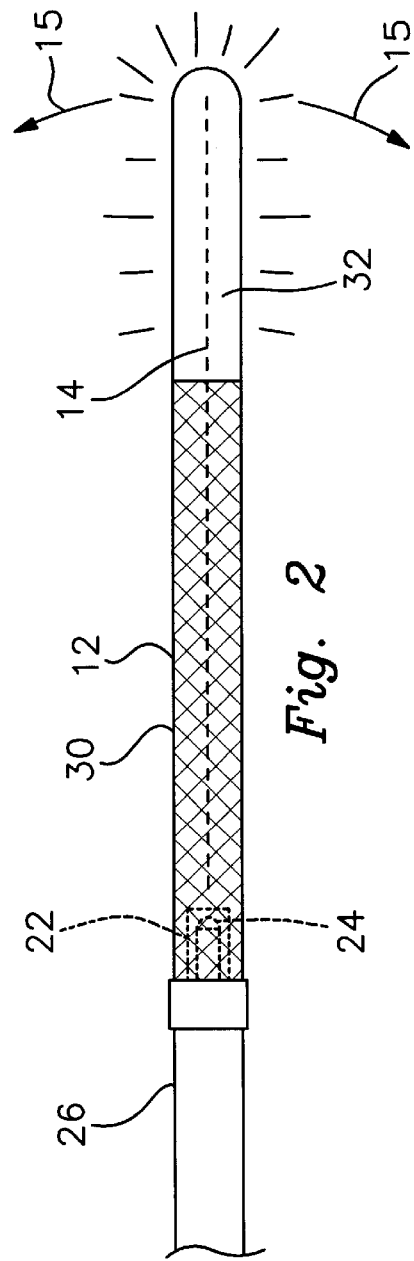
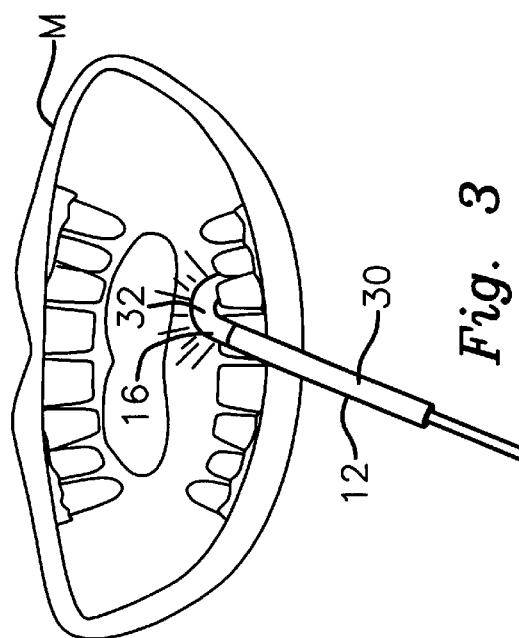

BENDABLE ILLUMINATING APPLIANCE

RELATED APPLICATION

This application is a continuation in part of U.S. Provisional Patent Application Serial No. 60/064,728 filed Nov. 6, 1997.

FIELD OF THE INVENTION

This invention relates to a medical, dental and surgical illuminating appliance and, more particularly, to a bendable light bar that is engaged with a fiberoptic light source to illuminate, for example, the interior of a dental patient's mouth.

BACKGROUND OF THE INVENTION

Dentists and oral surgeons often have a difficult time adequately illuminating the inside of a patient's mouth. Most dentists use an overhead lamp mounted on a pedestal and extending above the patient's chair. Usually, either the physician or an assistant must frequently adjust the lamp to illuminate the region of the mouth where dental or surgical work is being performed. Such adjustments are required because the patient's head may move or the dentist may have to work on a different tooth or in a different location in the mouth. Each time the position of the light needs to be changed, the dental procedure is interrupted. The dentist must then reposition the lamp himself or provide appropriate instructions to his assistant. In either event, manual manipulation of the dental lamp is time consuming and annoying. Moreover, standard overhead dental lamps are located a distance from the mouth and typically do not provide optimal illumination. At present, such lights are only able to illuminate a 28 mm surface within the mouth. This limited area of lighting usually necessitates even further adjustments of the light.

Presently, fiberoptic illuminators are widely employed in medical and surgical procedures. However, dentists and oral surgeons only occasionally utilize such illuminators. These instruments typically feature a headlamp that is worn by the physician and tethered by a fiberoptic cable to a light source. Dentists performing work inside the patient's mouth normally dislike wearing an item that ties or tethers them to another instrument. Such an arrangement restricts their freedom of movement during the dental procedure. Furthermore utilizing standard fiberoptic illumination systems requires the purchase and introduction of expensive and sometimes bulky equipment into the dental office. Nondental surgical headlamps exhibit similar disadvantages.

Fiberoptic lighting has also been attached to dental mirrors used directly inside the patient's mouth. Unfortunately, such illuminated dental mirrors are rather bulky and seriously limit the physician's working area within the mouth. Additionally, these appliances cannot be rested in the patient's mouth, and instead, must be constantly held and manipulated by the dentist or surgeon. Fiberoptically lighted mirrors too are tethered to a light source and tend to restrict the wearer's movement.

Shadowing and other lighting problems are also commonly experienced during nondental surgery. Conventional surgical illumination is often bulky and awkward to operate. Available lamps tend to interfere with the surgeon's view and are not readily adjustable. A need exists for an improved light that does not block the surgeon's view and is adjustable for use in various surgical environments.

SUMMARY OF INVENTION

It is therefore an object of this invention to provide an illuminating appliance that quickly, simply and effectively illuminates the interior of a patient's mouth and other body cavities without tethering the physician to standard fiberoptic illumination equipment and restricting his or her movement.

It is a further object of this invention to provide a medical and dental illuminating appliance that projects light into a patient's mouth or into a surgical body cavity with much greater intensity and effectiveness than is accomplished using standard lamps.

It is a further object of this invention to provide an oral cavity illuminating appliance that eliminates the interruption, inconvenience and annoyance that normally accompany having to frequently adjust an overhead dental lamp to properly illuminate selected areas of a patient's mouth.

It is a further object of this invention to provide medical and dental illuminating appliance that is relatively inexpensive, readily disposable, and easy to assemble, disassemble and replace, such that each successive patient is provided with a fresh, germ-free appliance.

It is a further object of this invention to provide a medical illuminating appliance having a readily adjustable shape that permits the device to be engaged securely and effectively at various positions within a patient's mouth or surgical body cavity.

It is a further object of this invention to provide an illuminating appliance that is readily adjustable into a variety of light projecting configurations so that a selected pattern of light may be broadcast within a patient's oral or other body cavity.

It is a further object of this invention to provide an oral cavity-illuminating appliance that achieves significantly improved lighting, particularly on the inside surfaces of the teeth and gums.

It is a further object of this invention to provide an oral cavity-illuminating appliance that assists effectively in diagnosing and detecting diseases, growths and lesions on the tongue, gums and soft tissue within the oral cavity.

It is a further object of this invention to provide an illuminating appliance that provides improved lighting for a wide variety of medical, dental and surgical procedures and which may be adjustably configured to engage and be used with various types of medical and surgical equipment.

It is a further object of this invention to provide an illuminating appliance that may be quickly and conveniently positioned and configured by the physician to properly illuminate a medical procedure.

This invention results from a realization that significantly improved lighting of the inside of a dental patient's mouth or a surgical patient's body cavity is achieved by projecting light into the mouth or other cavity through a light conducting rod that is communicably interconnected to a light source by a fiberoptic cable. This invention results from the further realization that by constructing such a light-conducting rod to be adjustably bendable, it can be effectively engaged at various locations within the patient's mouth or proximate a surgical cavity.

The invention features a bendable illuminating appliance that includes an elongate, substantially solid light conducting rod or bar. The rod is interconnected to a source of fiberoptic light by a light conductor. Means are carried by the rod for projecting light from the rod. The light-conducting rod is bendable and includes means for sustaining a shape into which the rod is bent.

In a preferred embodiment, the fiberoptic light conductor is a fiberoptic cable or optical fiber, which includes an outlet.

The light-conducting rod may be communicably connected to an inlet that is operably interconnected to the outlet of the fiberoptic light conductor such that light from the light source is transmitted through the light conductor and into the light-conducting rod. Preferably the light-conducting rod comprises a translucent material exclusively.

The means for projecting may include a portion or all of the exterior surface of the light-conducting rod. The light projecting means may more specifically include a rounded, bulbous or angled tip portion of the rod. The bulbous tip portion may include a concave, light projecting surface or indent that focuses the projected light onto a predetermined focal point. The angled tip portion may include a light-projecting surface that broadcasts light from the rod in a predetermined angle. At least a portion of the rod may be frosted or otherwise coated to minimize radial diffusion or dispersion of light projected from that portion of the rod.

The rod may include an elongate, flexible shaping element that maintains a selected shape into which the rod is flexed or bent. This permits the rod to be bent or formed into a hook shape so that it properly and comfortable engages the patient's mouth. Alternatively, in surgical applications, the rod may be engaged with and held by surgical equipment (e.g. a retractor) located proximate the portion of the patient's body cavity which is being examined. In alternative embodiments, the rod may comprise a flexible material that sustains the shape into which the rod is bent.

DETAILED DESCRIPTION OF PREFERRED EMBODIMENTS

Other objects, features and advantages will occur from the following description of preferred embodiments and the accompanying drawings, in which:

FIG. 2 is an elevational side view of the light-conducting rod in a straightened condition;

FIG. 3 is an elevational, perspective and partly schematic view of the illuminating appliance engaged with a dental patient's mouth, such that the interior of the mouth is illuminated;

Figure 1:
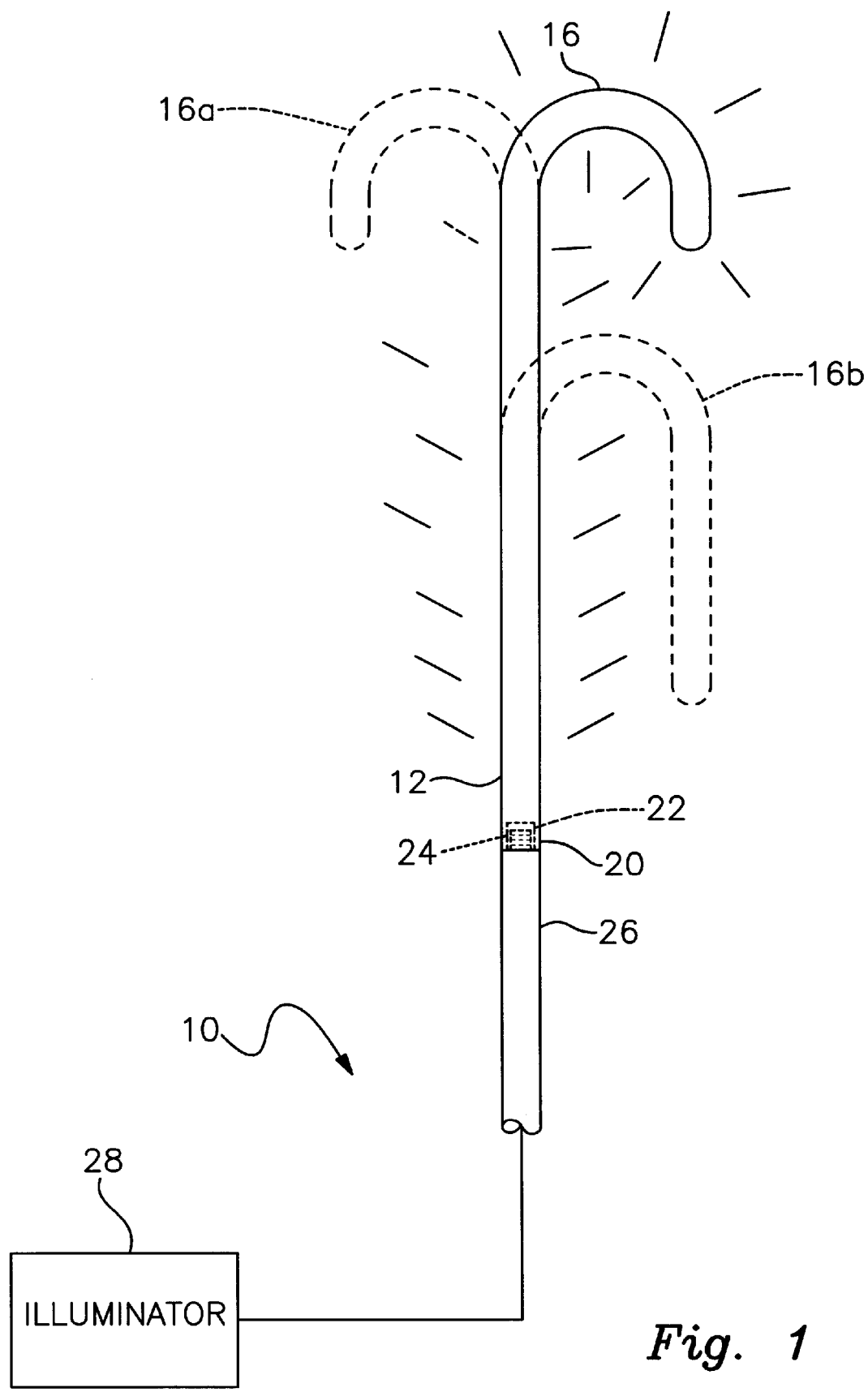
FIG. 1 is an elevational, partly schematic view of the bendable illuminating appliance of this invention; alternative flexed configurations of the apparatus are shown in phantom.

There is shown in FIG. 1 a medical, dental and surgical illuminating appliance 10. In dental applications the appliance is used to illuminate the interior of a patient's mouth so that appropriate dental work or other medical or surgical work may be performed within the oral cavity. Illuminator 10 includes a disposable rod 12. The rod comprises an elongate, substantially solid piece of a transparent or at least translucent light conducting plastic material. Rod 12 is lightweight and bendable. Various known sterile plastics, of the type presently used in medical surgical and dental procedures, may be employed. The plastic material comprising the rod should be appropriate for use in a patient's mouth or proximate a surgical body cavity.

As shown in FIG. 2, a bendable wire element 14 may be formed internally through rod 12. Alternatively, the entire rod itself may comprise a bendable or malleable material. In either event, rod 12 should be capable of being flexed, in the manner best shown in FIG. 1, to form a hook 16. The wire 14 or malleable plastic material composing rod 12 permits the rod to maintain its hook or otherwise bent shape until the user selectively straightens the rod or otherwise changes its shape. As further shown in FIG. 1, rod 12 may be bent in various degrees to form, for example, hooks 16a or 16b. These particular hooks are not a limitation of the invention, however, and a wide variety of alternative hooks and other rod configurations may be formed. In certain embodiments, rod 12 may be permitted to retain its straight, elongate shape, as shown in FIG. 2. In either event, rod 12 is initially formed to extend in a straight manner. It then may be flexed or bent as indicated by arrows 15, FIG. 2, to assume the generally hook-like shape depicted in FIG. 1.

A first, proximal end 20 of rod 12 includes a light inlet 22. As shown in FIGS. 1 and 2, inlet 22 communicably receives the discharge end fitting 24 of a standard fiberoptic conductor 26. This conductor may comprise an optical fiber or a fiberoptic cable. The opposite end of conductor 26 is operably connected to a conventional fiberoptic illuminator 28. When the illuminator is operated, light is directed through conductor 26 to light conducting rod 12. It should be understood that, instead of illuminator 28 may feature various types of light sources, including halogen and xenon. A wide variety of other light sources may also be employed in conjunction with light conducting rod 12. Additionally, it should be understood that numerous types of known fiberoptic fittings may be employed for operably and communicably interconnecting conductor 26 and rod 12. In the version shown herein, inlet 22 comprises a female fitting that receives discharge port 24. In alternative embodiments, the light-conducting rod may include a male fitting that interengages a female fitting carried by the light conductor cable. A threaded interconnection may also be made between the fiberoptic conductor and the lightconducting rod. In the disclosed embodiment, the inlet is unitarily connected to the rod and includes a translucent, light conducting material. This provides for significantly improved light transmission from conductor 26 to rod 12.

Illuminator 28 is activated so that light is transmitted through cable or fiber 26. This light is then transmitted through inlet 22 to light conducting rod 12. In certain embodiments (for example FIG. 1) the entire outer surface of the rod comprises a light projecting material. As a result, light is emitted from the rod along the entire length of the rod. In certain other embodiments, the outer surface of rod 12 may contain a frosting or coating 30, FIGS. 2 and 3, which reduces dispersion or diffusion of emitted light from rod 12. In such cases, light is projected only from the unfrosted or uncoated portion 32 of rod 12. This is typically the portion that is formed into a hook (see FIG. 3) and installed in the patient's mouth. In cases where a coating or frosting is employed, a portion of the rod (typically located at the distal or terminal end of the rod) does not carry the coating and acts as a light projector. In still other embodiments, the coating may be entirely eliminated and a transparent, light conducting material that inherently exhibits minimal radial light dispersion may be used. Likewise, in this embodiment, a distal or other portion of the rod should exhibit a light projecting capability.

Figure 4:
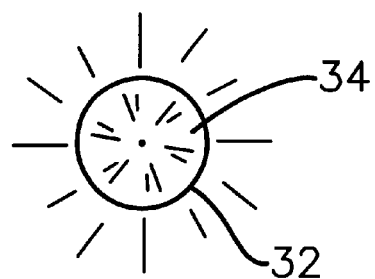
FIG. 4 is an elevational end view of the tip of the light-conducting rod.
Figure 5:
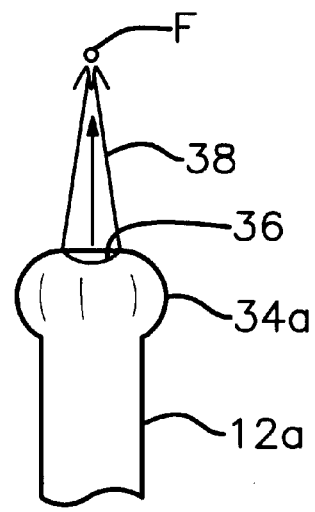
FIG. 5 is an elevational view of an alternative tip portion, which includes a light focusing indentation.
Figure 6:
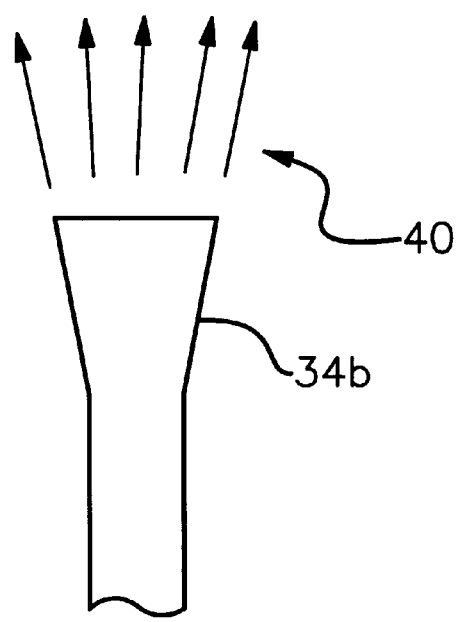
FIG. 6 is an elevational view of another alternative tip portion, which broadcasts an angled beam of light.

In the embodiment of FIGS. 2 and 4, light projecting portion 32 includes a rounded tip end 34. Light is projected from this portion in a uniform manner so that the inside of the oral cavity is uniformly illuminated. Alternative light projecting tips are depicted in FIGS. 5 and 6. For example, in FIG. 5, light-conducting rod 12a includes a rounded or bulbous tip portion 34a. A concave indent 36 is formed at the distal end of bulbous tip 34a. In such versions, the entire rod, with the exception of indent 36, is frosted or otherwise coated with a material that minimizes light dispersion. As a result, light rays 38 are directed by concave indent 36 toward a focal point F. This may comprise a point within the oral cavity (such as on the teeth, gums, tongue or soft tissue), or within a surgical cavity, which requires illuminated examination.

An alternative, angular light projecting tip 34b is shown in FIG. 5. That tip diverges from the rod and broadcasts light 40 over an angular range of approximately 20 degrees. Once again, particular medical, dental and/or surgical applications within the patient's mouth may make such broadcast lighting desirable. Various other types of tip configurations may be employed in order to accomplish selected types of lighting within the oral or other (i.e. surgical) body cavity.

Initially, the dentist or oral surgeon determines the particular type, location and intensity of lighting desired within the oral cavity. Then, rod 12 is bent, as indicated by arrows 15 in FIG. 2, into a desired hook shape. See FIG. 1. Rod 12 is engaged, in the manner shown in FIG. 3, with the patient's mouth M. Particularly, hook portion 16 is engaged with the patient's lips, teeth and gums. Illumination from light projecting portion 32 is directed onto the area of the oral cavity requiring examination. In surgical applications, rod 12 may be hung from or otherwise engaged with surgical equipment (such as a retractor) located proximate the patient's body cavity. In certain applications the sterile illuminating rod may be engaged with the surgical cavity itself.

The dentist, surgeon or other medical personnel may readily adjust the selected configuration and position of rod 12 so that optimal lighting is achieved. For example, the rod may be positioned to provide lighting toward the rear of the oral cavity or against the backside of the teeth or gums. Normally, it is very difficult to light such areas. The present invention permits the interior of the patient's mouth and oral cavity to be brightly illuminated. The dentist or surgeon can then perform necessary procedures within the oral cavity. Light is projected from an appliance directly within the patient's mouth. Constant adjustment of a remote dental lamp and the annoying interruptions that typically accompany this procedure are avoided.

The appliance of this invention provides for improved diagnosis of diseases and other medical or dental problems occurring in the oral cavity and, in particular, in the tongue, soft tissue, gums and/or teeth. The device is also effective for fully illuminating a surgical cavity. The shape adjustability of rod 12 allows the surgeon to position the light so that shadowing of tissue is minimized, and the surgeon's vision is not blocked. The adjustability also allows the light to be conveniently mounted proximate the area being examined. The device is particularly effective for use in procedures where suction is not required. The rod is constructed of a disposable, low cost material, which minimizes the risk that germs will be transmitted from patient to patient.

It will thus be seen that the objects made apparent from the preceding description are sufficiently obtained and certain changes may be made in the above construction without departing from the scope of the invention. It is intended that all matter contained in the above description and shown in the accompanying drawings be interpreted as illustrative and not in an imitative sense. Although specific features of the invention are shown in some drawings and not others, this is for convenience only as each feature may be combined with any or all of the features in accordance with the invention. Other embodiments, within the scope of this invention, will occur to those skilled in the art and are encompassed within the following claims.

What is claimed is:

1. An appliance for use in combination with a light source to illuminate the body cavity of a medical or dental patient, said appliance comprising:

a fiberoptic conductor having a proximal first end for operably engaging the light source and an opposite, distal end that carries a discharge end fitting; and an elongate, substantially solid rod composed of a light conducting material and having an inlet fitting for communicably and releasably receiving said discharge end fitting of said fiberoptic conductor, whereby light from the light source is transmitted through said fiberoptic light conductor and said inlet fitting into said rod for conduction therethrough, said rod being longitudinally bendable and having means for sustaining said rod in a selected shape into which said rod is bent, said rod further including an exterior surface that comprises a light projecting material for directing light conducted through the rod into the patient's body cavity.

2. The appliance of claim 1 in which said light conducting rod includes a translucent material exclusively.

3. The appliance of claim 1 in which said rod includes a light projecting rounded tip formed at one end of said rod, said inlet being formed at an opposite end of said rod.

4. The appliance of claim 1 in which said rod includes an angled tip portion having a light projecting surface that broadcasts light from the rod in a predetermined angle, said angled tip portion being formed at one end of said rod and said inlet being formed at an opposite end of said rod.

5. The appliance of claim 1 in which said rod includes a bulbous tip portion formed at one end of said rod, said bulbous tip portion having a concave, light projecting surface that focuses projected light onto a predetermined focal point, said inlet being formed at an opposite end of said rod.

6. The appliance of claim 1 in which at least a portion of the exterior surface of said rod includes means for minimizing the amount of conducted light projected from said rod.

7. The appliance of claim 1 in which said means for sustaining includes an elongate, flexible shaping element that maintains a selected shape into which said rod is bent.

8. The appliance of claim 1 in which said rod includes exclusively a malleable material that sustains the shape into which said rod is bent.

9. The appliance in claim 1 in which said inlet fitting is unitarily connected to said rod.

10. The appliance of claim 1 in which said exterior surface is partly frosted to restrict light dispersion from said rod.

11. The appliance of claim 1 in which said rod comprises a translucent, solid plastic rod.

12. An appliance for use in combination with a light source to illuminate the body cavity of a medical or dental patient, said appliance comprising:

a fiberoptic conductor having a proximal first end for operably engaging the light source and an opposite distal end that carries a discharge end fitting;

an elongate, solid plastic rod composed of a translucent material exclusively, said rod having an inlet fitting formed unitarily in a first end of said rod for communicably and releasably receiving said discharge end fitting of said fiberoptic conductor, whereby light from the light source is transmitted through said fiberoptic light conductor and said inlet fitting into said rod for conduction therethrough, said rod being longitudinally bendable; and means for sustaining said rod in a selected shape into which said rod is bent, said rod further comprising an exterior surface that includes light projecting material, at least proximate the end of said rod opposite said inlet fitting, for directing light conducted through said rod into the patient's body cavity.

13. An appliance for use in combination with a light source and a fiberoptic conductor to illuminate the body cavity of a medical or dental patient, said fiberoptic conductor having a proximal first end for operably engaging the light source and an opposite, distal end that carries a discharge end fitting, said appliance comprising:

an elongate, solid plastic rod composed of a translucent material exclusively, said rod having an inlet fitting formed unitarily in a first end of said rod for communicably and releasably discharging the discharge end fitting of the fiberoptic conductor, whereby light from the light source is transmitted through the fiberoptic light conductor and said inlet fitting into said rod for conduction therethrough, said rod being longitudinally bendable; and means for sustaining said rod in a selected shape into which said rod is bent, said rod further comprising an exterior surface that includes a light projecting material, at least proximate the end of said rod opposite said inlet fitting, for directing light conducted through said rod into the patient's body cavity.

* * * * *

UNITED STATES PATENT AND TRADEMARK OFFICE
CERTIFICATE OF CORRECTION

PATENT NO. : 6,304,712 B1
DATED : October 16, 2001
INVENTOR(S) : James M. Davis

It is certified that error appears in the above-identified patent and that said Letters Patent is hereby corrected as shown below:

Column 6,
Line 17, between "having means" and "for sustaining" insert -- contained within said rod --;

Column 7,
Line 1, between "means" and "for sustaining" insert -- contained within said rod --;

Column 8,
Line 8, between "means" and "for sustaining" insert -- contained within said rod --.
Beginning at line 15, add claims 14-16 as follows:
    14.    The appliance of claim 1 in which said rod is longitudinally exposed for the entire length of said rod such that light projects transversely therefrom.
    15.    The appliance of claim 12 in which said rod is longitudinally exposed for the entire length of said rod such that light projects transversely therefrom.
    16.    The appliance of claim 13 in which said rod is longitudinally exposed for the entire length of said rod such that light projects transversely therefrom.

Signed and Sealed this

Thirteenth Day of August, 2002

*Attest:*

JAMES E. ROGAN
*Attesting Officer*    *Director of the United States Patent and Trademark Office*